United States Patent
Seto

(10) Patent No.: US 9,726,654 B2
(45) Date of Patent: Aug. 8, 2017

(54) ATMOSPHERE SENSOR AND METHOD OF PRODUCING THE SAME, AND METHOD OF PRODUCING PRINTED MATTER

(71) Applicant: Masami Seto, Osaka (JP)

(72) Inventor: Masami Seto, Osaka (JP)

(73) Assignee: RICOH COMPANY, LTD., Tokyo (JP)

( * ) Notice: Subject to any disclaimer, the term of this patent is extended or adjusted under 35 U.S.C. 154(b) by 261 days.

(21) Appl. No.: 14/625,844

(22) Filed: Feb. 19, 2015

(65) Prior Publication Data
US 2015/0260673 A1 Sep. 17, 2015

(30) Foreign Application Priority Data
Mar. 14, 2014 (JP) .................. 2014-051616

(51) Int. Cl.
G01N 33/00 (2006.01)

(52) U.S. Cl.
CPC ................. *G01N 33/0059* (2013.01)

(58) Field of Classification Search
CPC ..... G01N 33/0059; G01N 2035/00465; G01N 1/2273; G01N 27/121
USPC ............ 73/23.2, 23.31, 25.03, 25.04, 25.05, 73/29.01, 29.05, 31.01, 31.02, 31.03, 73/31.05, 31.07; 205/788; 318/34
See application file for complete search history.

(56) References Cited

U.S. PATENT DOCUMENTS

| | | | |
|---|---|---|---|
| 9,285,251 B2 * | 3/2016 | Enquist | G01N 21/783 |
| 2003/0141529 A1 | 7/2003 | Seto et al. | |
| 2004/0183155 A1 | 9/2004 | Seto et al. | |
| 2005/0146004 A1 | 7/2005 | Seto | |
| 2006/0060939 A1 | 3/2006 | Seto et al. | |
| 2006/0144144 A1 | 7/2006 | Seto | |
| 2007/0022814 A1 | 2/2007 | Seto | |
| 2007/0037310 A1 | 2/2007 | Seto | |
| 2009/0263149 A1 | 10/2009 | Makino | |
| 2014/0079458 A1 * | 3/2014 | Seto | G03G 21/203 399/389 |
| 2014/0232780 A1 | 8/2014 | Seto | |
| 2014/0245814 A1 * | 9/2014 | Montanari | G01N 33/2841 73/19.1 |
| 2015/0011852 A1 * | 1/2015 | Van Kesteren | A61B 5/1491 600/326 |

FOREIGN PATENT DOCUMENTS

| | | |
|---|---|---|
| JP | 6-074646 | 3/1944 |
| JP | 63-119834 | 5/1988 |
| JP | 63-123421 | 5/1988 |
| JP | 63-123422 | 5/1988 |
| JP | 4-036648 | 2/1992 |
| JP | 6-288673 | 10/1994 |

(Continued)

*Primary Examiner* — Michael A Lyons
*Assistant Examiner* — Suman K Nath
(74) *Attorney, Agent, or Firm* — Cooper & Dunham LLP

(57) ABSTRACT

An atmosphere sensor includes a detecting element configured to detect external atmospheric characteristics of the atmosphere sensor. The atmosphere sensor includes inside a case having an opening, to contain the detecting element; and a moisture permeable film located on the opening to pass external water vapor of the atmosphere sensor. The moisture permeable film is bonded to the case by a welding method.

18 Claims, 11 Drawing Sheets

(56) References Cited

FOREIGN PATENT DOCUMENTS

| | | |
|---|---|---|
| JP | 7-019546 | 1/1995 |
| JP | 7-055748 | 3/1995 |
| JP | 7-120025 | 5/1995 |
| JP | 9-051790 | 2/1997 |
| JP | 9-273782 | 10/1997 |
| JP | 10-129308 | 5/1998 |
| JP | 11-351647 | 12/1999 |
| JP | 11-351648 | 12/1999 |
| JP | 11-351730 | 12/1999 |
| JP | 11-351731 | 12/1999 |
| JP | 11-351732 | 12/1999 |
| JP | 2000-046402 | 2/2000 |
| JP | 2000-193577 | 7/2000 |
| JP | 2000-292404 | 10/2000 |
| JP | 2001-330283 | 11/2001 |
| JP | 2002-039574 | 2/2002 |
| JP | 2002-310876 | 10/2002 |
| JP | 2002-372278 | 12/2002 |
| JP | 2003-070528 | 3/2003 |
| JP | 2003-181937 | 7/2003 |
| JP | 2004-031073 | 1/2004 |
| JP | 2004-068230 | 3/2004 |
| JP | 2004-271461 | 9/2004 |
| JP | 2004-279370 | 10/2004 |
| JP | 2005-052287 | 3/2005 |
| JP | 2006-058084 | 3/2006 |
| JP | 2009-000402 | 1/2009 |
| JP | 2009-000403 | 1/2009 |
| JP | 2009-002883 | 1/2009 |
| JP | 2009-133858 | 6/2009 |
| JP | 2009-258473 | 11/2009 |
| JP | 2011-102781 | 5/2011 |
| JP | 2011-133442 | 7/2011 |
| JP | 2012-068054 | 4/2012 |
| JP | 2013-194946 | 9/2013 |

* cited by examiner

ATMOSPHERE SENSOR AND METHOD OF PRODUCING THE SAME, AND METHOD OF PRODUCING PRINTED MATTER

CROSS-REFERENCE TO RELATED APPLICATIONS

This patent application is based on and claims priority pursuant to 35 U.S.C. §119 to Japanese Patent Application No. 2014-051616, filed on Mar. 14, 2014, in the Japan Patent Office, the entire disclosure of which is hereby incorporated by reference herein.

BACKGROUND

Technical Field

The present invention relates to an atmosphere sensor and a method of producing the same, and a method of producing a printed matter.

Description of the Related Art

Japanese Patent No. JP-5211821-B2 (JP-2009-258473-A) discloses an image forming apparatus detecting an atmospheric humidity near a paper with a humidity sensor and setting printing conditions based on the detected humidity.

The humidity sensor needs to expose its detecting element to an environmental atmosphere, and prevent it from being influenced by wind and being contaminated. Therefore, it is known that the detecting element is covered with a moisture permeable film which does not pass water, but passes water vapor.

It is conventionally known that the moisture permeable film is bonded to the humidity sensor with an adhesive. In this case, the adhesive unevenly applied between the humidity sensor and the moisture permeable film may cause insufficient contactness therebetween. Further, the contactness deteriorates as time passes and the moisture permeable film may peel off from the humidity sensor. In order to solve this problem, it is known that a non-woven fabric is overlapped with the moisture permeable film.

However, the non-woven fabric improves the contactness between the humidity sensor and the moisture permeable film, but the non-woven fabric and the adhesive absorb moisture, resulting in errors in measurement of humidity.

SUMMARY

Accordingly, one object of the present invention is to provide an atmosphere sensor capable of detecting atmospheric characteristics such as humidity with high preciseness.

Another object of the present invention is to provide a method of producing the atmosphere sensor.

A further object of the present invention is to provide a method of producing a printed matter using the atmosphere sensor.

These objects and other objects of the present invention, either individually or collectively, have been satisfied by the discovery of an atmosphere sensor, including a detecting element to detect external atmospheric characteristics of the atmosphere sensor, wherein the atmosphere sensor includes inside a case having an opening, to contain the detecting element; and a moisture permeable film located on the opening, to pass external water vapor of the atmosphere sensor, and wherein the moisture permeable film is bonded to the case by a welding method.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

DETAILED DESCRIPTION

Figure 1:
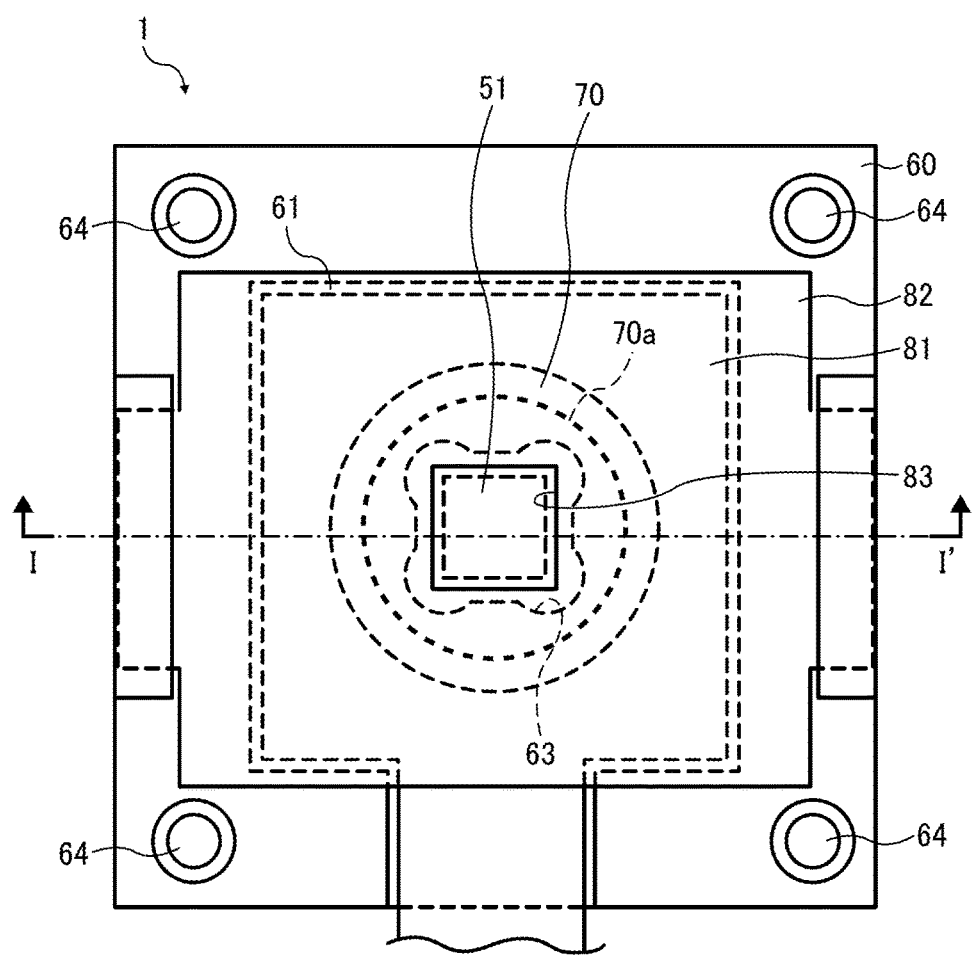
FIG. 1 is a top view illustrating a configuration of an embodiment 1 of a humidity detection sensor 1.

The present invention provides an atmosphere sensor capable of detecting atmospheric characteristics such as humidity with high preciseness.

Exemplary embodiments of the present invention are described in detail below with reference to accompanying drawings. In describing exemplary embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner and achieve a similar result. The same configurations have the same numbers.

FIG. 1 is a top view illustrating a configuration of an embodiment 1 of a humidity detection sensor 1. The humidity detection sensor 1 is an example of the atmosphere sensor.

Figure 5:
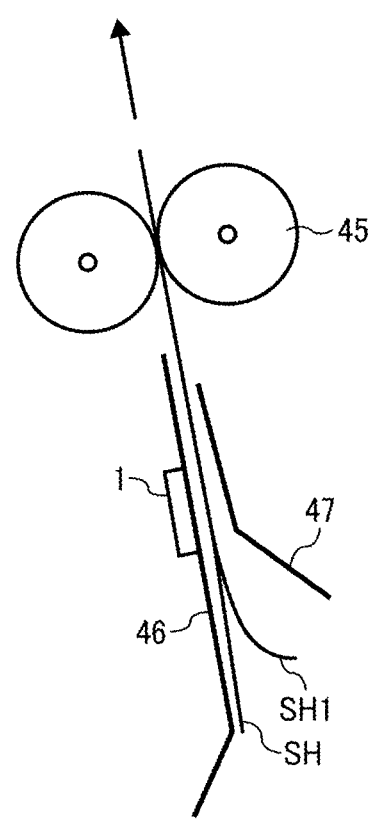
FIG. 5 is a schematic view illustrating a location of the humidity detection sensor 1 in the mage forming apparatus 100 in FIG. 4.
Figure 6:
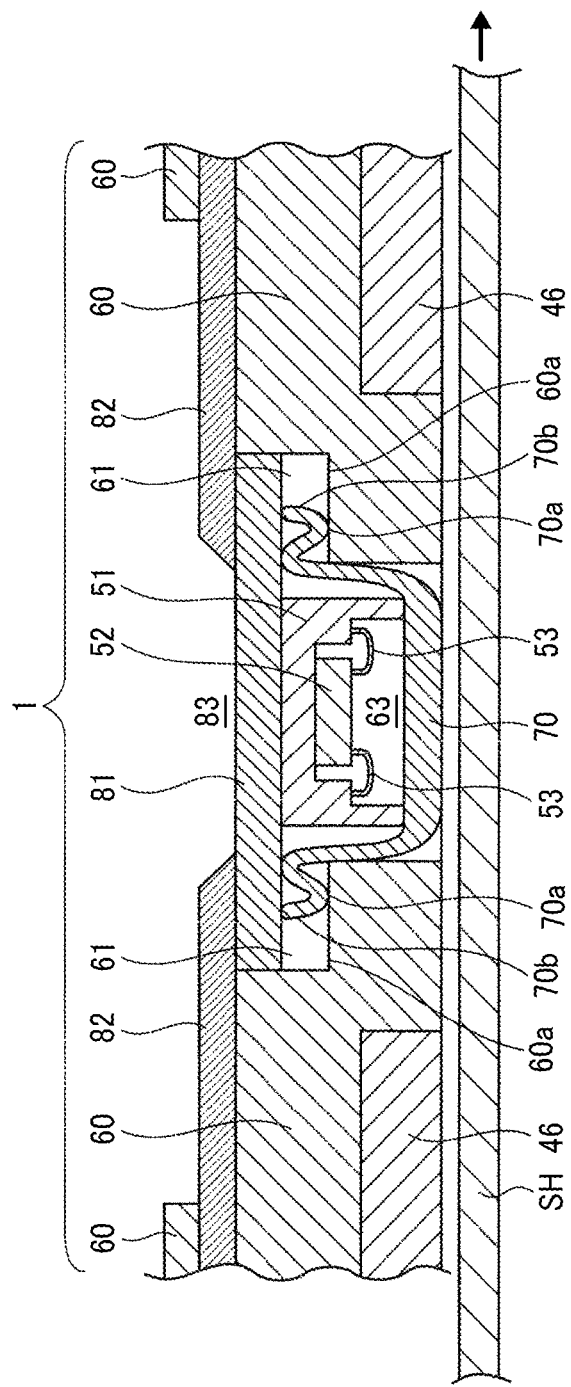
FIG. 6 is a longitudinal sectional view for explaining positional relations among the humidity detection sensor 1, a guide plate 46 and a sheet SH.

In FIG. 1, the humidity detection sensor 1 includes a sensor package 51, a sensor case 60, a moisture permeable film 70, a flexible substrate 81 and a cap 82. The sensor case 60 includes four tapped holes 64 to be screwed to a guide plate 46 (FIGS. 5 and 6). The moisture permeable film 70 has the shape of a circle or an oval. The sensor package 51 has the shape of a square. The length of a side thereof is, e.g., 3 mm. The sensor case 60 includes a concavity 61 on the top surface thereof. The concavity 61 includes an opening 63 at the center, which penetrates the sensor case 60 in a thickness direction thereof. The opening 63 has the shape of a square having four circular corners. The opening 63 is larger than the sensor package 51. The sensor package 51 is located at the center of the opening 63. The cap 82 includes an opening 83 at the center thereof. Right and left parts of the cap 82 are inserted into pockets formed on the sensor case 60 to be fixed thereon.

The sensor case 60 is formed of polyvinylchloride having thermoplasticity. The moisture permeable film 70 is formed of PTFE (polytetrafluoroethylene) having extensibility and porosity. The moisture permeable film 70 passes water vapor being a gas, but does not pass water being a liquid. The moisture permeable film 70 has a thickness of, e.g., 0.3 mm.

Figure 2:
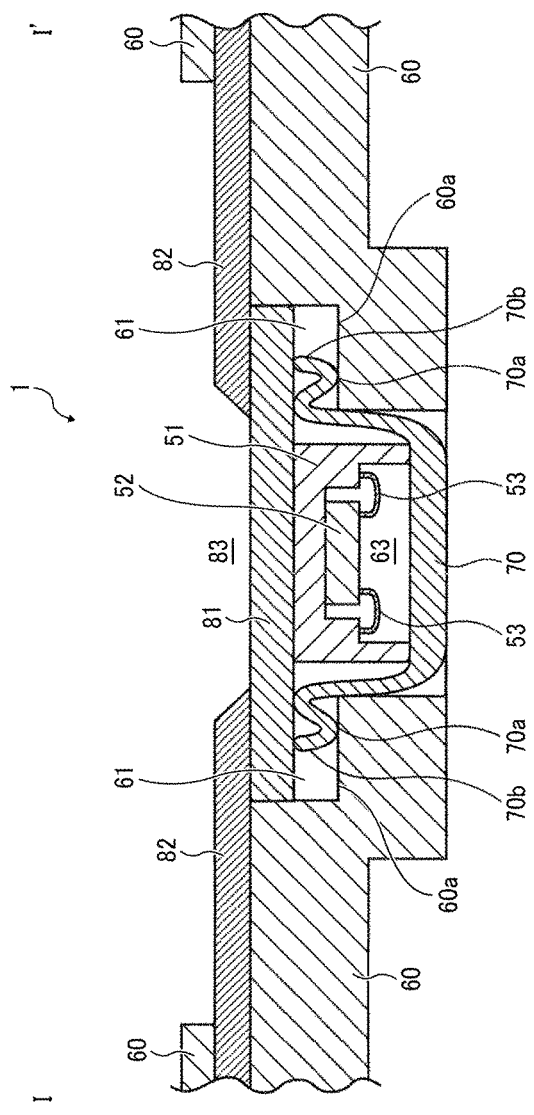
FIG. 2 is a longitudinal sectional view illustrating the humidity detection sensor 1 in FIG. 1 when cut through I to I'.

FIG. 2 is a longitudinal sectional view illustrating the humidity detection sensor 1 in FIG. 1 when cut through I to I'. In FIG. 2, the humidity detection sensor 1 further includes a humidity detection chip 52 and a wired 53.

The flexible substrate 81 and the sensor package 51 are bonded to each other. The sensor package 51 is hollow, and the humidity detection chip 52 is bonded to the inside of upper wall of the sensor package 51. The humidity detection chip 52 and the sensor package 51 are electrically connected with each other through the wire 53. The wire 53 is formed not to be out from an opening of the sensor package 51. The sensor package 51 has a wiring electrically connecting the wire 53 and the flexible substrate 81 with each other. The sensor package 51 includes an opening at the bottom surface thereof. The bottom surface is lower than the bottom surface 60a of the concavity 61.

A welded part 70a of the moisture permeable film 70 is bonded to the bottom surface 60a of the concavity 61 (the inner surface of the sensor case 60, which is opposite to the opening 63) by a heat-welding method. The moisture permeable film 70 blocks the opening of the sensor package 51.

The humidity detection chip 52 produces a signal having a signal level corresponding to an absolute humidity of air in the sensor package 51 and outputs the signal to the flexible substrate 81 through the wire 53 and the wiring of in the sensor package 51. The humidity detection chip 52 is embodied with a humidity sensor disclosed in Japanese Patent No. JP-2889909-B1 (JP-H07-055748-A). The humidity detection chip 52 is formed by MEMS (Micro Electro Mechanical System). The cap 82 pushes the flexible substrate 81 and the sensor package 51 into the sensor case 60. The moisture permeable film 70 is sandwiched between the flexible substrate 81 and the bottom surface 60a the moisture permeable film 70 is bonded to. The sensor case 60 has such a height and the concavity 61 has such a depth that there is no difference in level between the bottom surface of the moisture permeable film 70 and the bottom surface of the sensor case 60.

Figure 3:
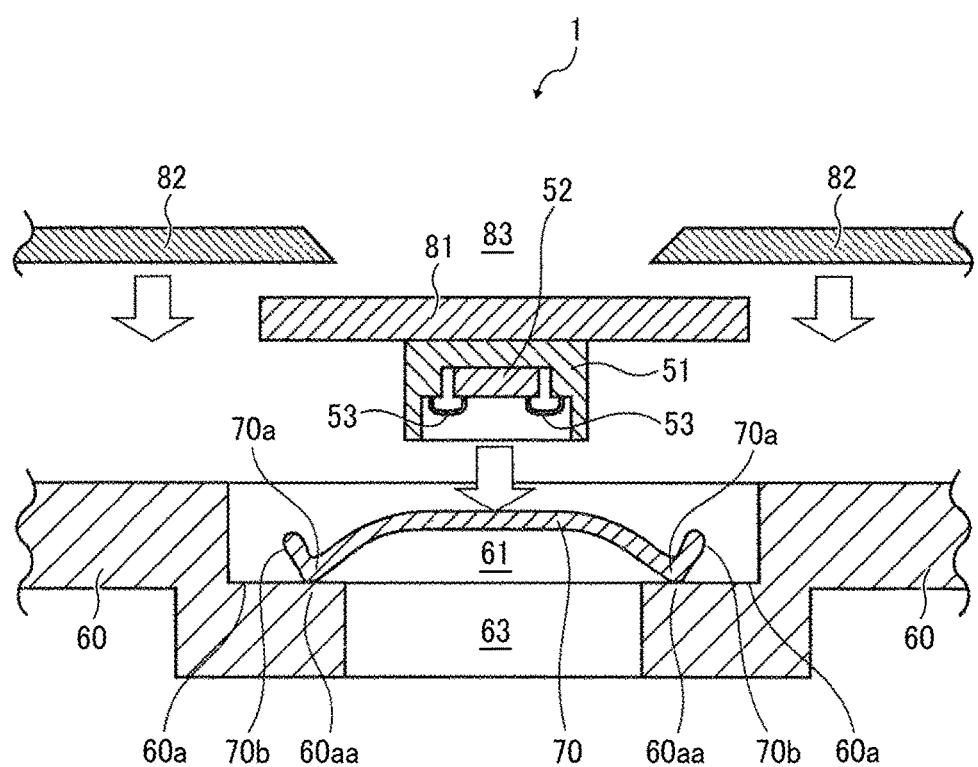
FIG. 3 is a longitudinal sectional view illustrating a method of constructing the humidity detection sensor 1 in FIG. 1.

FIG. 3 is a longitudinal sectional view illustrating a method of constructing the humidity detection sensor 1 in FIG. 1. The method is explained below.

In FIG. 3, the humidity detection chip 52 is die bonded to the sensor package 51, and the sensor package 51 is soldered to the flexible substrate 81. On the other hand, the moisture permeable film 70 is bonded to the sensor case 60 by a heat-welding method so as to block a lower opening of the sensor case 60. Specifically, the moisture permeable film 70 is placed on the bottom surface 60a of the concavity 61, and a heated metallic ring is pressed onto the welded part 70a of the moisture permeable film 70 toward the bottom surface 60a to melt a part 60aa of the bottom surface 60a of the sensor case 60 into the welded part 70a. Thus, the welded part 70a of the moisture permeable film 70 is bonded to the bottom surface 60a of the concavity 61. The heat-welding method includes heating at 250° C. for 5 sec. The heat-welding method bonds the moisture permeable film 70 to the sensor case 60 stronger than when bonded with an adhesive. The moisture permeable film 70 having the shape of a circle or an oval and the welded part 70a having the shape of a ring make bonded strength between the welded part 70a and the bottom surface 60a of the sensor case 60 uniform. Next, the flexible substrate 81 mounted with the sensor package 51 is inserted into the concavity 61. The concavity 61 fixes the flexible substrate 81 at a predetermined position in the sensor case 60. Then, the bottom surface of the sensor package 51 is pressed against the moisture permeable film 70. Having extensibility, the moisture permeable film 70 is pushed down by the sensor package 51 and adheres to the opening thereof.

An end 70b of the moisture permeable film 70 curls upward when the welded part 70a is bonded to the sensor case 60 by a heat-welding method. The flexible substrate 81 presses the curled 70b downward when pressed into the concavity 61. When the moisture permeable film 70 has a thickness of 0.3 mm, the concavity 61 has such a depth that a gap between the flexible substrate 81 and the bottom surface 60a of the concavity 61 is 0.33 mm.

In the humidity detection sensor 1 configured as above, bonded to the sensor case 60 by the heat-welding method, the moisture permeable film 70 is more difficult to peel from the sensor case 60 than when bonded with an adhesive. Since the moisture permeable film 70 covers the opening of the sensor package 51 without a non-woven fabric and an adhesive, the humidity detection sensor 1 more precisely detects an absolute humidity of the atmosphere than when the moisture permeable film 70 is bonded to the sensor package 51 with a non-woven fabric and an adhesive.

Figure 4:
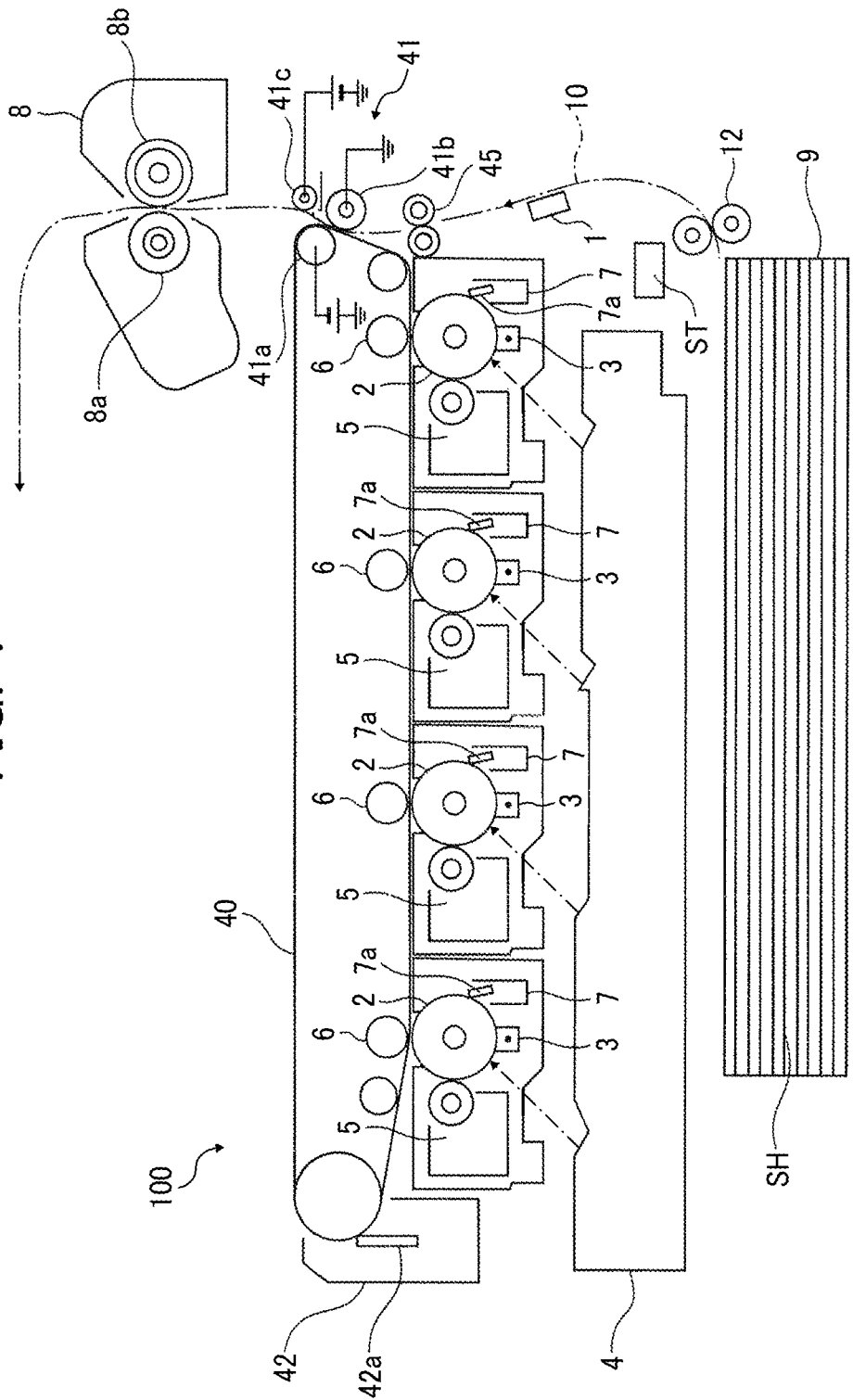
FIG. 4 is a schematic view illustrating a configuration of an image forming apparatus 100 including the humidity detection sensor 1 in FIG. 1.

FIG. 4 is a schematic view illustrating a configuration of an image forming apparatus 100 including the humidity detection sensor 1 in FIG. 1. The image forming apparatus 100 includes a second transferer capable of producing full-color images. The image forming apparatus 100 is an electrophotographic copier. In FIG. 4, the image forming apparatus 100 includes a photoconductor drum 2 as an image bearer, a charger 3, a writer (an irradiator) 4, an image developer 5, a first transferer 6 and a cleaner 7 for each color, i.e., cyan, yellow, magenta and black. The image forming apparatus 100 further includes an endless transfer belt 40 as a transferer, a second transferer 41, a cleaner 42, a fixer 8, a paper feeding cassette 9, a pair of rollers 12, a pair of registration rollers 45, a humidity detection sensor 1 and a controller ST. Each of the cleaners 7 includes a cleaning blade 7a, and the cleaner 42 includes a cleaning blade 42a. The fixer 8 includes a fixing roller 8a and a pressure roller 8b. The second transferer 41 includes a transfer rollers 41a and 41b, and a hold roller 41c.

The charger 3, the writer 4, the image developer 5, the first transferer 6 and the cleaner 7 are located around the photoconductor drum 2 for every color. The transfer belt 40 is located to contact the photoconductor drum 2. The cleaner 42 is located at a downstream side in the travel direction of the transfer belt 40. The second transferer 41 is located at an upstream side in the travel direction thereof. The fixer 8 is located above the second transferer 41. The humidity detection sensor 1 is located near the pair of registration rollers 45.

The paper feeding cassette 9 contains plural layered sheet materials SH. The sheet material SH is ejected through a pair of the rollers 12, a paper feeding conveyance path 10, a pair of the registration rollers, the second transferers 41 and the fixer 8. The sheet materials SH is a paper or a recording medium.

In the image forming apparatus 100 configured as above, the surface of the photoconductor drum 2 rotating at a predetermined process speed is uniformly charged by the charger 3. Next, according to image information of an original document read by a reader (unillustrated), the writer irradiates the surface of the photoconductor drum 2 to form an electrostatic latent image thereon. Next, the image developer 5 develops the electrostatic latent image with a toner (developer) to form a toner image on the surface of the photoconductor drum 2 for every color. The toner images of plural colors formed on the photoconductor drums 2 are sequentially transferred by the first transferer 6 on the transfer belt 40 rotating at a predetermined process speed to be overlapped thereon.

On the other hand, the sheet material SH is conveyed from the paper feeding cassette 9 at a predetermined timing to the second transferer 41 through the paper feeding conveyance path 10. The toner image borne by the transfer belt 40 is transferred onto the sheet material SH by the second transferer 41. The sheet material SH the toner image is transferred on is conveyed to the fixer 8 at a downstream side of the conveyance direction of the transfer belt 40, and heated and pressurized by the fixing roller 8a and the pressure roller 8b such that the toner image is fixed on the sheet material SH. The sheet material SH the toner image is fixed on is ejected out from the image forming apparatus 100 by a paper ejection roller (unillustrated).

The toner image remaining on the surface of the photoconductor drum 2, which has not been transferred onto the transfer belt 40, is removed by the cleaning blade 7a of the cleaner 7, and the surface of the photoconductor drum 2 is used for forming a following electrostatic latent image. The toner image remaining on the surface of the transfer belt 40, which has not been transferred onto the sheet material SH, is removed by the cleaning blade 42a of the cleaner 42, and the surface of the transfer belt 40 is used for forming a following electrostatic latent image.

The humidity detection sensor 1, as mentioned later in detail, detects an absolute humidity of an atmosphere near the sheet material SH fed from the paper feeding cassette 9. In addition, the humidity detection sensor 1 detects an absolute humidity of an atmosphere near a sheet material SH1 (cf. FIG. 5), on one side of which an image is formed, fed through the fixer 8. Further, the humidity detection sensor 1 detects an environmental humidity when the sheet material SH is not fed from the paper feeding cassette 9. As mentioned later in detail, the absolute humidity near the sheet material SH and the environmental humidity detected by the humidity detection sensor 1 are used to control the image forming apparatus 100.

FIG. 5 is a schematic view illustrating a location of the humidity detection sensor 1 in the mage forming apparatus 100 in FIG. 4.

In FIG. 5, the image forming apparatus 100 further includes guide plates 46 and 47 located near a pair of the registration rollers 45. The guide plates 46 and 47 guide the sheet material SH fed from the fed from the paper feeding cassette 9 and the sheet material SH1 conveyed through the fixer 8 to a pair of registration rollers 45. The humidity detection sensor 1 is fixed on the guide plate 46. Being formed using MEMS technology, a humidity detection chip 52 can be downsized to have a size about 1 mm×1 mm, and as a result, the humidity detection sensor 1 can be downsized as well. Therefore, the humidity detection sensor 1 can be located in comparatively a narrow space.

FIG. 6 is a longitudinal sectional view for explaining positional relations among the humidity detection sensor 1, the guide plate 46 and the sheet SH.

In FIG. 6, the guide plate 46 has an opening penetrating the plate in a thickness direction thereof. The humidity detection sensor 1 is fixed on the guide plate 46 in such a way that a lower part of the humidity detection sensor 1 is stored in the opening of the guide plate 46. The sensor case 60 and the guide plate 46 are formed such that there is no difference in level between the bottom surface of the humidity detection sensor 1 and that of the guide plate 46 when the humidity detection sensor 1 is fixed thereon. The humidity detection sensor 1 fixed on the guide plate 46 locate itself near the sheet material SH at a regular distance apart therefrom.

A technical significance of bonding the moisture permeable film 70 in the humidity detection sensor 1 in the embodiment is explained. When the moisture permeable film 70 is bonded on the bottom surface of the humidity detection sensor 1 by the heat-welding method, the end 70b of the moisture permeable film 70 curls downward. Therefore, a distance between the bottom surface of the humidity detection sensor 1 and the sheet material SH needs to enlarge extra so as not to contact the curled end 70b to the sheet material SH. This worsens detection preciseness of the absolute humidity near the sheet material SH. However, when the moisture permeable film 70 is bonded to an inside of the sensor case 60, the curled end 70b of the moisture permeable film 70 does not come out from the bottom surface of the sensor case 60. Therefore, the distance between the humidity detection sensor 1 and the sheet material SH can be shorter than when the moisture permeable film 70 is bonded on the bottom surface of the humidity detection sensor 1. This enables the humidity detection sensor 1 to more precisely detect the absolute humidity near the sheet material SH than when the moisture permeable film 70 is bonded on the bottom surface of the humidity detection sensor 1.

Figure 7:
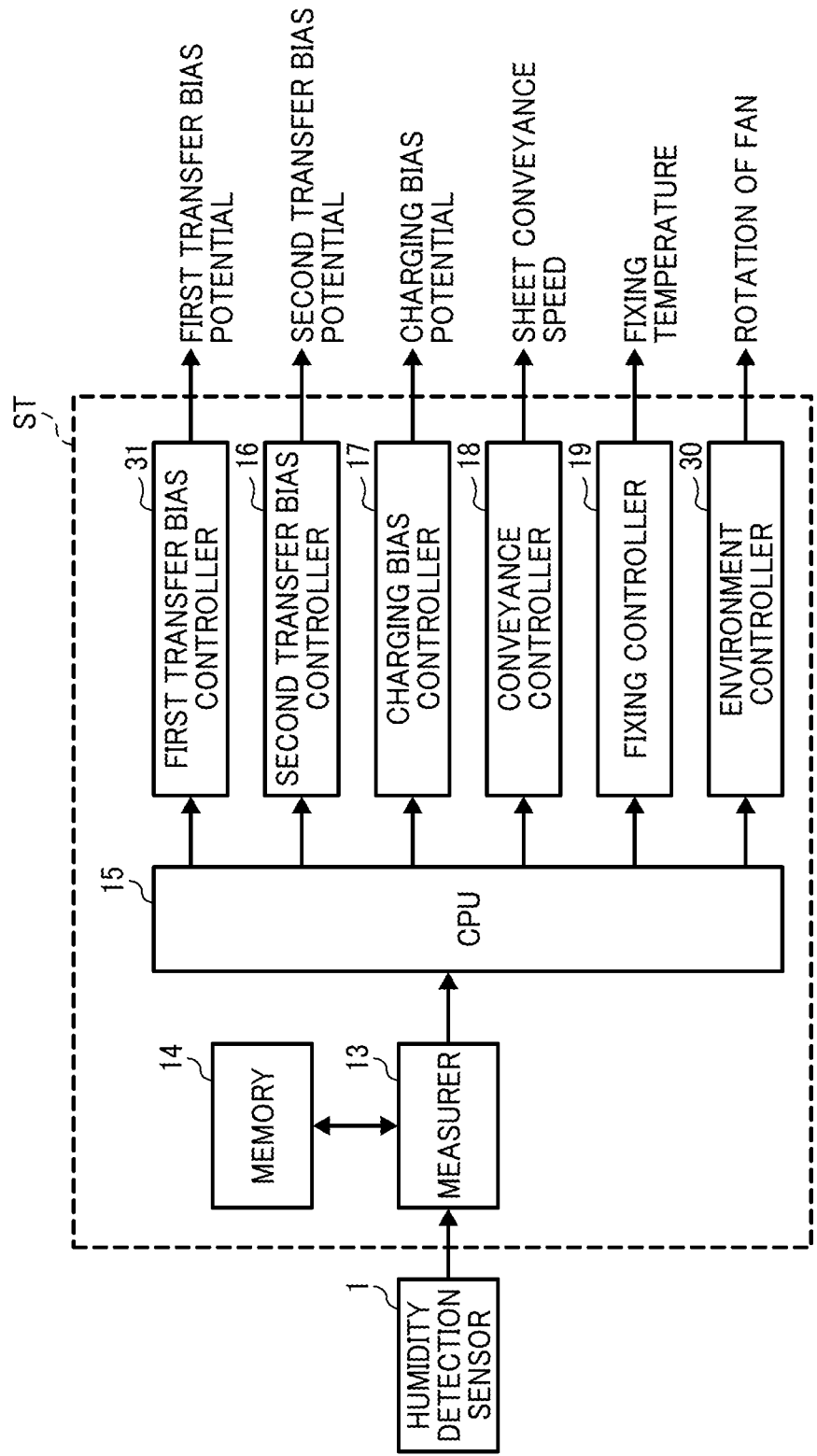
FIG. 7 is a block diagram showing a configuration of a controller ST in FIG. 5.

FIG. 7 is a block diagram showing a configuration of the controller ST in FIG. 5.

In FIG. 7, the controller ST includes a measurer 13, a memory 14, a CPU 15, a first transfer bias controller 31, a second transfer bias controller 16, a charging bias controller 17, a conveyance controller 18, a fixing controller 19 and an environment controller 30.

The humidity detection sensor 1 produces a detected output at the measurer 13, and the measurer 13 transmits and receives information to and from the memory 14 and produces the result at the CPU 15. The CPU 15 works as a controller controlling all operations in the image forming apparatus 100. In addition, the CPU 15 controls the first transfer bias controller 31, the second transfer bias controller 16, the charging bias controller 17, the conveyance controller 18, the fixing controller 19 and the environment controller 30, based on information entered from the measurer 13. The first transfer bias controller 31 controls a first transfer bias potential, the second transfer bias controller 16 controls a second transfer bias potential, the charging bias controller 17 controls a charging bias potential, and the conveyance controller 18 controls a conveyance speed of the sheet material SH. The fixing controller 19 controls a fixing temperature, and the environment controller 30 controls a rotational number of a fan (unillustrated) located in the image forming apparatus 100.

The memory 14 previously stores data showing relation between the environmental humidity and the absolute humidity of the atmosphere near the sheet material SH. The measurer 13 measures or calculates the absolute humidity of the atmosphere near the sheet material SH fed from the paper feeding cassette 9, based on the detection result produced from the humidity detection sensor 1 and the data previously memorized in the memory 14.

The CPU 15 controls the first transfer bias controller 31, the second transfer bias controller 16, the charging bias controller 17, the conveyance controller 18 and the fixing controller 19, based on the absolute humidity of the atmosphere near the sheet material SH produced from the measurer 13. The CPU 15 controls the fixing controller 19 to increase the fixing temperature of a toner when the absolute humidity of the atmosphere near the sheet material SH is high, and decrease the fixing temperature of a toner when the absolute humidity of the atmosphere near the sheet material SH is low. Thus, the CPU 15 sets image forming conditions such as the fixing temperature of a toner and the conveyance speed, which are preferable for the sheet material SH. Further, the CPU 15 controls the environment controller 30, based on the environmental humidity produced from the measurer 13 to control a fan motor rotating the fan in the image forming apparatus 100. Specifically, the CPU 15 controls the fan to exhaust air in the image forming apparatus 100 when the environmental humidity is high. Details of these controls are disclosed in Japanese Patent No. JP-5211821-B1 (JP-2009-258473-A), and explanations thereof are omitted.

In the humidity detection sensor 1 of the image forming apparatus 100, the moisture permeable film 70 is bonded to the sensor case 60 by the heat-welding method. Therefore, the moisture permeable film 70 is more difficult to peel from the humidity detection sensor 1 than when bonded with an adhesive. Since the moisture permeable film 70 blocks the opening of the sensor package 51 without a non-woven fabric and an adhesive, the humidity detection sensor 1 more precisely detects the absolute humidity of the atmosphere near the sheet material SH than when bonded to the sensor package 51 with a non-woven fabric and an adhesive. The curled end 70b of the moisture permeable film 70 does not come out from the bottom surface of the sensor case 60 because the moisture permeable film 70 is bonded to an inside of the sensor case 60. Therefore, the distance between the humidity detection sensor 1 and the sheet material SH can be shorter than when the moisture permeable film 70 is bonded on the bottom surface of the humidity detection sensor 1, and the absolute humidity near the sheet material SH can be more precisely detected.

The image forming apparatus 100 sets image forming conditions preferable for the sheet material, based on the absolute humidity of the atmosphere near the sheet material SH to form an image thereon. Therefore, an image formed on the sheet material SH improves in quality more than an image formed by a conventional method. Further, the image forming apparatus 100 controls image forming conditions, based on the absolute humidity of the atmosphere near the sheet material SH, which is detected by the humidity detection sensor 1 to form an image having improved in quality more than an image formed by a conventional method thereon.

Figure 8:
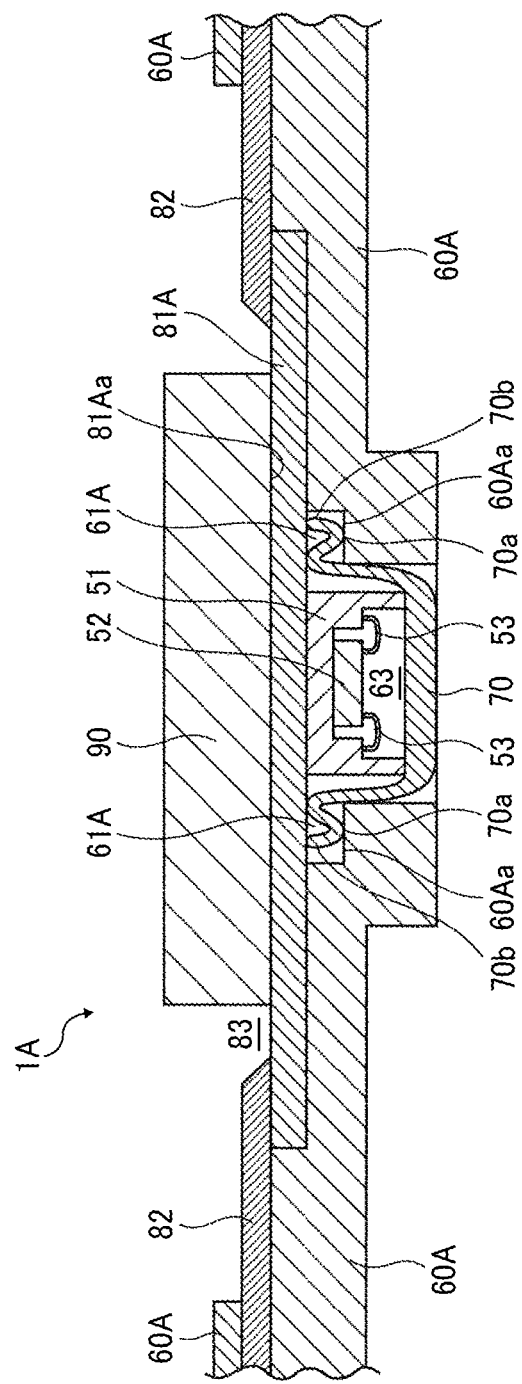
FIG. 8 is a longitudinal sectional view illustrating a configuration of a humidity detection sensor 1A of a modified example of embodiment 1.

FIG. 8 is a longitudinal sectional view illustrating a configuration of a humidity detection sensor 1A of a modified example of embodiment 1.

In FIG. 8, the humidity detection sensor 1A of a modified example of embodiment 1 is different from the humidity detection sensor 1 in the following points:

(1) including a flexible substrate 81A instead of the flexible substrate 81;

(2) including a sensor case 60A instead of the sensor case 60; and (3) further including a signal processing circuit 90.

The differences are explained below.

In FIG. 8, the flexible substrate 81A has a wider width than the flexible substrate 81 in FIG. 2. The sensor case 60A has a concavity 61A at the top surface. The concavity 61A has a larger width only at a part storing the flexible substrate 81A. A signal processing circuit 90 is mounted in an opening 83 of a cap 82 near a humidity detection chip 52 on a surface 81Aa a sensor package 51 is not mounted on (the surface opposite to an opening 63 of the flexible substrate 81A). The signal processing circuit 90 includes, e.g., a signal amplifying circuit, a heater drive circuit and/or an A/D converting circuit. The signal processing circuit 90 controls the humidity detection chip 52 and processes a signal produced therefrom.

As mentioned above, the modified example locates the signal processing circuit 90 closer to the humidity detection chip 52 than embodiment 1 to prevent noises from mixing in signals transmitted and received between the signal processing circuit 90 and the humidity detection chip 52.

Figure 9:
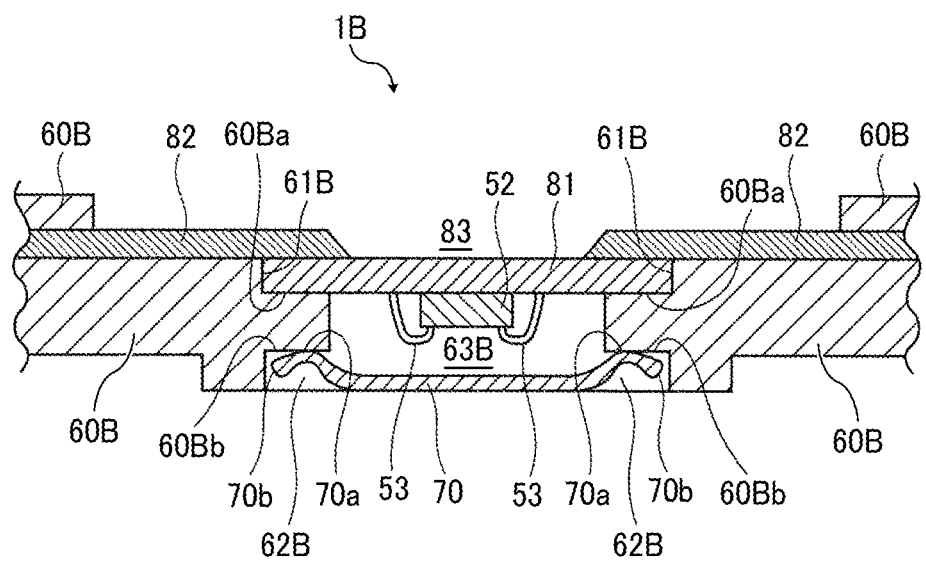
FIG. 9 is a longitudinal sectional view illustrating a configuration of a humidity detection sensor 1B of an embodiment 2.

FIG. 9 is a longitudinal sectional view illustrating a configuration of a humidity detection sensor 1B of an embodiment 2.

In FIG. 9, the humidity detection sensor 1B is different from the humidity detection sensor 1 in the following points:

(1) including no sensor package 51; and (2) including a sensor case 60B instead of the sensor case 60.

The differences are explained below.

In FIG. 9, a humidity detection chip 52 is bonded to the bottom surface of a flexible substrate 81, and they are electrically connected with each other by a wire 53.

The sensor case 60B has a concavity 61B at the top surface, a concavity 62B at the bottom surface and an opening 63B penetrating from the bottom surface 60Ba of the concavity 61B to the undermost surface of the concavity 62B. The concavity 61B has a depth equivalent to a thickness of the flexible substrate 81. A welded part 70a of a moisture permeable film 70 is bonded to the bottom surface 60Bb of the concavity 62B (inner surface of the sensor case 60B and a surface at the side of the opening 63B) by the heat-welding method.

An end 70b of a moisture permeable film 70 curls downward due to the heat-welding method. The concavity 61B has such a depth that the curled end 70b is above the bottom surface of the sensor case 60B. A distance between the bottom surface of the humidity detection sensor 1B and a sheet material SH can be shorter than when there is no concavity 62B to improve detection preciseness of an absolute humidity near the sheet material SH.

Figure 10:
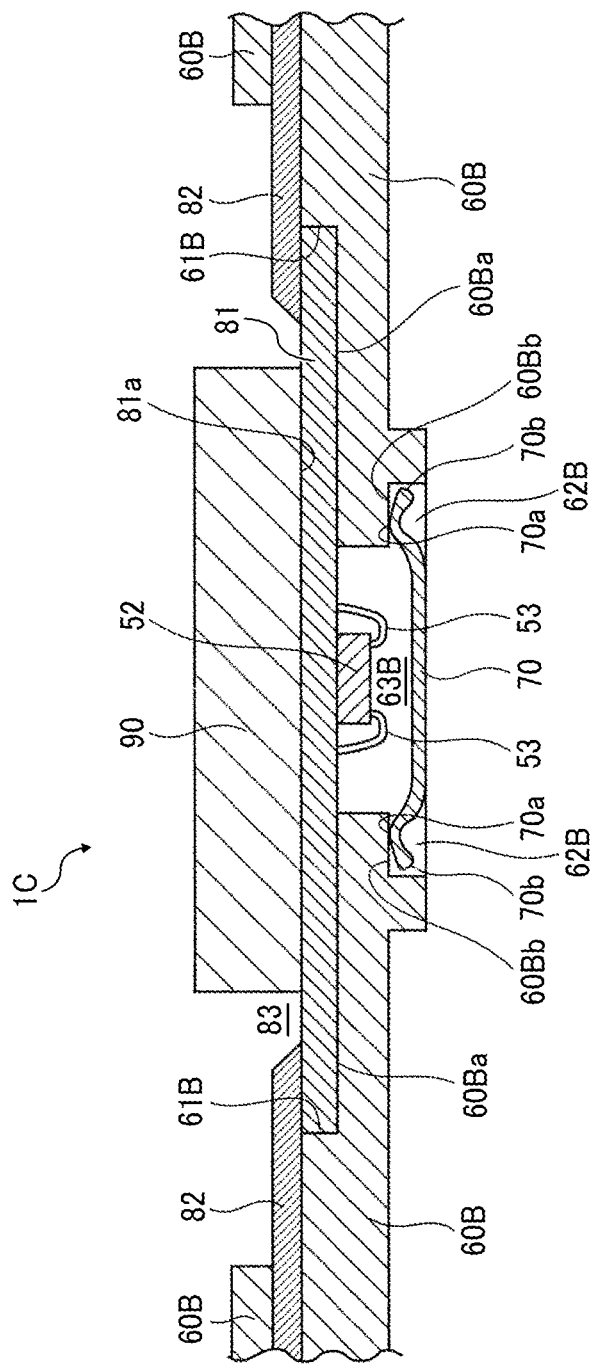
FIG. 10 is a longitudinal sectional view illustrating a configuration of a humidity detection sensor 1C of a modified example of embodiment 2.

FIG. 10 is a longitudinal sectional view illustrating a configuration of a humidity detection sensor 1C of a modified example of embodiment 2.

In FIG. 10, the humidity detection sensor 1C is different from the humidity detection sensor 1B in FIG. 10 in further including a signal processing circuit 90.

The differences are explained below.

In FIG. 10, a signal processing circuit 90 is mounted in an opening 83 of a cap 82 near a humidity detection chip 52 on a surface 81a a humidity detection chip 52 is not mounted on (the surface opposite to an opening 63B of a flexible substrate 81). The signal processing circuit 90 includes, e.g., a signal amplifying circuit, a heater drive circuit and/or an A/D converting circuit. The signal processing circuit 90 controls the humidity detection chip 52 and processes a signal produced therefrom. As mentioned above, the modified example locates the signal processing circuit 90 closer to the humidity detection chip 52 than embodiment 2 to prevent noises from mixing in signals transmitted and received between the signal processing circuit 90 and the humidity detection chip 52.

The embodiment 1 uses the humidity detection sensor 1 to configure the image forming apparatus 100. The present invention is not limited thereto, and may use one of the humidity detection sensors 1A, 1B and 1C to configure the image forming apparatus 100.

In each of the above embodiments, the sensor case 60 is formed of polyvinylchloride, but the present invention is not limited thereto and the sensor case 60 may be formed of thermoplastic resins besides polyvinylchloride such as ABS resins.

In each of the above embodiments, the moisture permeable film 70 is formed of PTFE, but the present invention is not limited thereto and the moisture permeable film 70 may be formed of a member passing gas and no liquid besides PTFE.

In each of the above embodiments, the moisture permeable film 70 has the shape of a circle or n oval, but the present invention is not limited thereto and the moisture permeable film 70 may have the shape of a square besides the shape of a circle or n oval.

In each of the above embodiments, the sensor package 51 has the shape of a square, but the present invention is not limited thereto and the sensor package 51 may have the shape of a circle or a rectangle beside the shape of a square.

In each of the above embodiments, the flexible substrate 81 is used, but the present invention is not limited thereto and a print substrate may be used.

In each of the above embodiments, the image forming apparatus 100 is an electrophotographic copier, but the present invention is not limited thereto and the image forming apparatus 100 may be an image forming apparatus besides the electrophotographic copier.

In each of the above embodiments, the humidity permeable film 70 is bonded to the sensor case 60 by a heat-welding method, but the present invention is not limited thereto and it may be bonded thereto by a spin welding method, an oscillation welding method, an ultrasonic welding method, a high-frequency welding method or a semiconductive laser welding method.

In each of the above embodiments, the humidity detection sensor 1 detects an absolute humidity of an atmosphere near the sheet SH, but the present invention is not limited thereto and it may detect an absolute humidity of an atmosphere near an object such as concretes, foods, plants or organic skins besides the sheet SH.

In each of the above embodiments, the atmospheric sensor is the humidity detection sensor 1, but the present invention is not limited thereto and it may detect a concentration, a thermal conductivity or a temperature of a gas besides a humidity.

In embodiment 1, the humidity detection sensor 1 is located such that there is no difference in level between the bottom surface of the moisture permeable film 70 and the bottom surface of the sensor case 60, but the present invention is not limited thereto and it may be located such that there is a difference in level therebetween.

In embodiment 1, the opening 63 has the shape in FIG. 1, but the present invention is not limited thereto and it may have a shape besides the shape therein such as the shape of a square.

In modified examples of embodiment 1 and embodiment 2, the signal processing circuit 90 controls the humidity detection chip 52 and processes a signal produced therefrom, but the present invention is not limited thereto and it may not control the humidity detection chip 52.

Figure 11A:
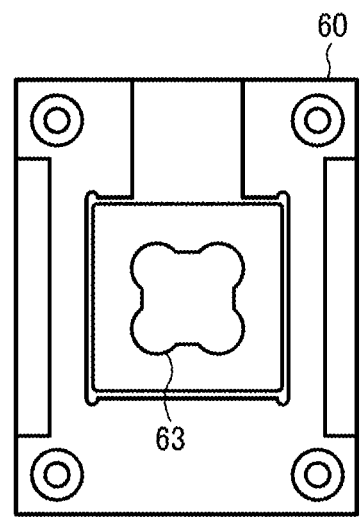
FIG. 11A is a top view illustrating an example of a sensor case 60 of embodiment 1.
Figure 11B:
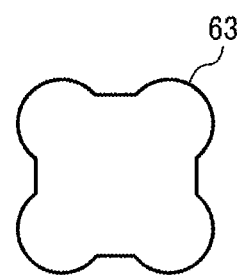
FIG. 11B is a top view illustrating a detailed shape of an opening 62 of the sensor case 60 in FIG. 11A.

FIG. 11A is a top view illustrating an example of a sensor case 60 of embodiment 1. FIG. 11B is a top view illustrating a detailed shape of an opening 62 of the sensor case 60 in FIG. 11A. In FIGS. 11A and 11B, the unit is mm. In FIG. 11B, an opening 63 has the shape of a square having circular shapes at four corners.

Having now fully described the invention, it will be apparent to one of ordinary skill in the art that many changes and modifications can be made thereto without departing from the spirit and scope of the invention as set forth therein.

What is claimed is:

1. An atmosphere sensor, comprising a substrate and a detecting element disposed on the substrate and configured to detect external atmospheric characteristics in a vicinity of the atmosphere sensor,
wherein the atmosphere sensor comprises inside:
a case having an opening and an inner surface, and configured to contain the detecting element; and
a moisture permeable film covering the opening, configured to pass water vapor external to the atmosphere sensor, and
wherein the moisture permeable film is bonded to the case by a welding method, and
wherein the substrate sandwiches the moisture permeable film with the inner surface to which the moisture permeable film is bonded.

2. The atmosphere sensor of claim 1, wherein the atmospheric characteristics are of humidity, temperature, thermal conductivity or gas concentration.

3. The atmosphere sensor of claim 1, wherein the moisture permeable film is bonded to the inner surface of the case at an opening side of the case.

4. The atmosphere sensor of claim 1, wherein the moisture permeable film is bonded to the inner surface of the case at an opposite side of the case, the opposite side being opposite to an opening side of the case opening.

5. The atmosphere sensor of claim 1, further comprising:
a signal processing circuit,
wherein the substrate has an opening and an inner surface, and
the signal processing circuit is located on the inner surface of the substrate opposite to an outer surface of the substrate and is configured to process a signal from the detecting element.

6. The atmosphere sensor of claim 1, wherein the moisture permeable film has the shape of a circle or an oval.

7. The atmosphere sensor of claim 1, wherein the atmospheric characteristics are of humidity, temperature, thermal conductivity or gas concentration; and the moisture permeable film is bonded to the inner surface of the case at an opening side of the case.

8. The atmosphere sensor of claim 1, wherein the atmospheric characteristics are of humidity, temperature, thermal conductivity or gas concentration; and the moisture permeable film is bonded to the inner surface of the case at an opposite side of the case, the opposite side being opposite to an opening side of the case.

9. The atmosphere sensor of claim 1, further comprising:
a signal processing circuit,
wherein the substrate has an opening and an inner surface, and
the signal processing circuit is located on the inner surface of the substrate opposite to an outer surface of the substrate and is configured to process a signal from the detecting element,
wherein the moisture permeable film is bonded to the inner surface of the case at an opposite side of the case, the opposite side being opposite to an opening side of the case.

10. The atmosphere sensor of claim 1, further comprising:
a signal processing circuit,
wherein the substrate has an opening and an inner surface, and
the signal processing circuit is located on the inner surface of the substrate opposite to an outer surface of the substrate and is configured to process a signal from the detecting element, and
wherein the atmospheric characteristics are of humidity, temperature, thermal conductivity or gas concentration; the moisture permeable film is bonded to an inner surface of the case at an opposite side of the case, the opposite side being opposite to an opening side of the case.

11. The atmosphere sensor of claim 1, wherein the atmospheric characteristics are of humidity, temperature, thermal conductivity or gas concentration; and the moisture permeable film has the shape of a circle or an oval.

12. The atmosphere sensor of claim 1, wherein the moisture permeable film is bonded to the inner surface of the case at an opening side of the case; and the moisture permeable film has the shape of a circle or an oval.

13. The atmosphere sensor of claim 1, wherein the moisture permeable film is bonded to the inner surface of the case at an opposite side of the case, the opposite side being opposite to an opening side of the case; and the moisture permeable film has the shape of a circle or an oval.

14. The atmosphere sensor of claim 1, wherein the atmospheric characteristics are of humidity, temperature, thermal conductivity or gas concentration; the moisture permeable film is bonded to the inner surface of the case at an opposite side of the case, the opposite side being opposite to an opening side of the case; and the moisture permeable film has the shape of a circle or an oval.

15. The atmosphere sensor of claim 1, wherein the atmospheric characteristics are of humidity, temperature, thermal conductivity or gas concentration; the moisture permeable film is bonded to the inner surface of the case at an opposite side of the case, the opposite side being opposite to an opening side of the case; and the moisture permeable film has the shape of a circle or an oval.

16. The atmosphere sensor of claim 1, further comprising:
a signal processing circuit,
wherein the substrate has an opening and an inner surface, and
the signal processing circuit is located on the inner surface of the substrate opposite to an outer surface of the substrate and configured to process a signal from the detecting element, wherein the atmospheric characteristics are of humidity, temperature, thermal conductivity or gas concentration; the moisture permeable film is bonded to the inner surface of the case at an opposite side of the case, the opposite side being opposite to an opening side of the case; and the moisture permeable film has the shape of a circle or an oval.

17. A method of producing an atmosphere sensor that includes a substrate and a detecting element disposed on the substrate and configured to detect external atmospheric characteristics in a vicinity of the atmosphere sensor inside and a case having an opening and an inner surface, said method comprising:
producing the atmosphere sensor by bonding a moisture permeable film that passes water vapor external to the atmosphere sensor, to the case by a welding method so as to cover the opening with the moisture permeable film, wherein the substrate sandwiches the moisture permeable film with the inner surface to which the moisture permeable film is bonded.

18. A method of producing printed matter with an image forming apparatus including an atmosphere sensor, the atmosphere sensor comprising:
a substrate;
a detecting element disposed on the substrate and configured to detect external atmospheric characteristics in the vicinity of the atmosphere sensor;
a case having an opening and an inner surface, and configured to contain the detecting element; and
a moisture permeable film bonded on the case by a welding method and covering the opening, configured to pass water vapor external to the atmosphere sensor,
wherein the substrate sandwiches the moisture permeable film with the inner surface to which the moisture permeable film is bonded, and
wherein the method comprises controlling image forming conditions used to produce the printed matter based on a signal from the atmosphere sensor, and producing the printed matter in accordance with said image forming conditions.

* * * * *